US012562275B2

(12) United States Patent
Kwon et al.

(10) Patent No.: US 12,562,275 B2
(45) Date of Patent: Feb. 24, 2026

(54) INTERACTIVE SUBGROUP DISCOVERY

(71) Applicants: International Business Machines Corporation, Armonk, NY (US); The General Hospital Corporation, Boston, MA (US)

(72) Inventors: Bum Chul Kwon, Cambridge, MA (US); Uri Kartoun, Cambridge, MA (US); Shaan Syed Khurshid, Cambridge, MA (US); Steven Alan Lubitz, Newton, MA (US); Kenney Ng, Arlington, MA (US)

(73) Assignees: International Business Machines Corporation, Armonk, NY (US); The Broad Institute, Inc., Cambridge, MA (US)

( * ) Notice: Subject to any disclaimer, the term of this patent is extended or adjusted under 35 U.S.C. 154(b) by 901 days.

(21) Appl. No.: 17/497,852

(22) Filed: Oct. 8, 2021

(65) Prior Publication Data

US 2023/0112063 A1 Apr. 13, 2023

(51) Int. Cl.
| | |
|---|---|
| *G06N 20/00* | (2019.01) |
| *G06N 3/00* | (2023.01) |
| *G16H 40/67* | (2018.01) |
| *G16H 50/20* | (2018.01) |
| *G16H 50/30* | (2018.01) |
| *G16H 50/70* | (2018.01) |

(52) U.S. Cl.
CPC .............. *G16H 50/20* (2018.01); *G06N 3/00* (2013.01); *G06N 20/00* (2019.01); *G16H 40/67* (2018.01); *G16H 50/30* (2018.01); *G16H 50/70* (2018.01)

(58) Field of Classification Search
CPC ........ G16H 50/20; G16H 40/67; G16H 50/30; G16H 50/70; G16H 50/50
See application file for complete search history.

(56) References Cited

U.S. PATENT DOCUMENTS

| | | |
|---|---|---|
| 7,634,503 B2 | 12/2009 | Venugopal |
| 8,150,849 B2 | 4/2012 | Chaudhury |
| 10,861,028 B2 | 12/2020 | Silberman |
| (Continued) | | |

OTHER PUBLICATIONS

Peter Mell and Timothy Grance, The NIST Definition of Cloud Computing, NIST Special Publication 800-145, cover, pp. i-iii, 1-3, Sep. 2011.

(Continued)

*Primary Examiner* — Sanchita Roy
(74) *Attorney, Agent, or Firm* — Caleb Wilkes; Otterstedt & Kammer PLLC

(57) ABSTRACT

Obtain covariates and an outcome data for a population. Partition the population into a plurality of subgroups. Produce outcomes predictions by applying a machine learning model to the covariate data for the population. Establish performance measures based on the outcomes predictions. Compare the performance measures for at least one subgroup to the performance measures for at least one other subgroup. Identify an outlying subgroup for which the machine learning model produces performance measures that are different than the performance measures for one or more other subgroups. Optionally, retrain the machine learning model on additional covariate and outcomes data for the outlying subgroup.

20 Claims, 10 Drawing Sheets

(56) References Cited

U.S. PATENT DOCUMENTS

| | | | |
|---|---|---|---|
| 2005/0192954 A1 | 9/2005 | Gupta | |
| 2012/0123948 A1 | 5/2012 | Fefer | |
| 2018/0165697 A1 | 6/2018 | Stolorz | |
| 2019/0148024 A1* | 5/2019 | Zhong | A61M 5/1723 |
| | | | 705/2 |
| 2020/0364245 A1 | 11/2020 | Sinha | |
| 2020/0380310 A1 | 12/2020 | Weider | |
| 2021/0125730 A1* | 4/2021 | Lefkofsky | G06N 20/00 |
| 2021/0201190 A1* | 7/2021 | Edgar | G06N 20/00 |
| 2023/0008904 A1* | 1/2023 | Venkataraman | G06N 20/00 |

OTHER PUBLICATIONS

Atmueller, "Semi-Automatic Visual Subgroup Mining using Vikamine," Journal of Universal Computer Science, vol. 11, No. 11 (Nov. 2005), p. 1752-1765.

Dingen, "RegressionExplorer: Interactive Exploration of Logistic Regression Models with Subgroup Analysis," IEEE Transactions on Visualization and Computer Graphics, vol. 25, No. 1, Jan. 2019, p. 246-255.

Ballarini et al., "SubgrPlots: Graphical Displays for Subgroup Analysis in Clinical Trials", https://rdrr.io/cran/SubgrPlots/, Jan. 29, 2020, 02 pages (archived copy of original NPL reference #2 filed in IDS dated Jan. 3, 2022).

Ballarini et al., "Supplementary Material Part 2: R code for reproducing the figures in the manuscript for a Critical Review of Graphics for Subgroup Analyses in Clinical Trials and Some Improvements", from https://rdrr.io/cran/SubgrPlots/, Jan. 29, 2020, 31 pages.

No Author "Cran Package SubgrPlots", Aug. 27, 2025, 01 page, https://cran.r-project.org/web/packages/SubgrPlots/index.html (showing that original NPL reference #2 filed in IDS dated Jan. 3, 2022 is no longer available at cited location).

* cited by examiner

500 →

| CIRCULATORY (139,807) | | | | | | | | ALL PATIENTS (439,393) | | | | | | | |
|---|---|---|---|---|---|---|---|---|---|---|---|---|---|---|---|
| VARIABLE | OUTCOME YES | OUTCOME YES SD | N_YES | OUTCOME NO | OUTCOME NO SD | N_NO | P_VALUE | VARIABLE | OUTCOME YES | OUTCOME YES SD | N_YES | OUTCOME NO | OUTCOME NO SD | N_NO | P_VALUE |
| AGE_AT_INDEX_DATE | 63.347319 | 5.361517 | 6386 | 60.941649 | 6.2726241 | 133421 | 0 | AGE_AT_INDEX_DATE | 63.071316 | 5.4815091 | 7395 | 58.511297 | 6.8358902 | 431998 | 0 |
| C2HEST | 0.8855628 | 0.8605683 | 1125 | 0.8278982 | 0.7192776 | 17059 | 0.00055 | C2HEST | 0.8031102 | 0.8403318 | 1140 | 0.4185922 | 0.616253 | 21243 | 0 |
| CHA2DS2_VASC | 1.7420821 | 1.1621986 | 3465 | 1.8404614 | 1.0234653 | 70566 | 1.15E-06 | CHA2DS2_VASC | 1.6275862 | 1.1592423 | 3683 | 1.1480539 | 0.8978318 | 124964 | 0 |
| CHARGE_AF | 12.714786 | 0.7480269 | 6386 | 12.307314 | 0.8296035 | 133421 | 0 | CHARGE_AF | 12.643822 | 0.7629432 | 7395 | 11.849517 | 0.8862985 | 431998 | 0 |
| DBP_AT_INDEX_DATE | 83.02208 | 11.117602 | 6386 | 84.214531 | 10.569491 | 133421 | 4.99E-19 | DBP_AT_INDEX_DATE | 82.907708 | 10.935262 | 7395 | 82.465848 | 10.076777 | 431998 | 0.001406361 |
| EHR_AF | 7.3183593 | 0.62614 | 6386 | 6.9324505 | 0.677682 | 133421 | 0 | EHR_AF | 7.2744343 | 0.6312189 | 7395 | 6.6176752 | 0.7230271 | 431998 | 0 |
| HEIGHT_AT_INDEX_DAT | 170.99148 | 9.2020335 | 6380 | 107.99407 | 9.297210 | 133421 | 0 | HEIGHT_AT_INDEX_DAT | 171.14064 | 9.2949489 | 7395 | 108.0845 | 9.2136889 | 431998 | 5.34E-177 |
| IS_AFIB:YES | 1 | - | - | 0 | - | - | 0 | IS_AFIB:YES | - | - | - | 0 | - | - | 0 |
| IS_CEREBRAL_ATHEROS | 0.0284998 | - | - | 0.0175361 | - | - | 6.39E-11 | IS_CEREBRAL_ATHEROS | 0.0254226 | - | - | 0.0068033 | - | - | 5.47E-79 |
| IS_CHD:YES | 0.1202136 | - | - | 0.0803507 | - | - | 6.40E-28 | IS_CHD:YES | 0.1103448 | - | - | 0.0291506 | - | - | 0 |
| IS_CHF:YES | 0.0281867 | - | - | 0.0117448 | - | - | 1.36E-30 | IS_CHF:YES | 0.0243408 | - | - | 0.0037963 | - | - | 1.00E-162 |
| IS_CKD:YES | 0.0139367 | - | - | 0.0080497 | - | - | 6.06E-07 | IS_CKD:YES | 0.0121704 | - | - | 0.0028982 | - | - | 6.75E-46 |
| IS_DM:YES | 0.0735965 | - | - | 0.0665977 | - | - | 2.58E-05 | IS_DM:YES | 0.0649087 | - | - | 0.0244932 | - | - | 6.75E-107 |
| IS_HYPERLIPIDEMIA:Y | 0.302067 | - | - | 0.2923378 | - | - | 0.09791 | IS_HYPERLIPIDEMIA:Y | 0.2742394 | - | - | 0.564475 | - | - | 2.29E-166 |
| IS_HYPERTENSION:YES | 0.5917632 | - | - | 0.6105036 | - | - | 0.00283 | IS_HYPERTENSION:YES | 0.5284652 | - | - | 0.3037259 | - | - | 0 |
| IS_HYPOTHYRODISM:YE | 0.0646508 | - | - | 0.0671034 | - | - | 0.00011 | IS_HYPOTHYRODISM:YE | 0.0534145 | - | - | 0.0549702 | - | - | 0.57794127 |
| IS_MALE:YES | 0.6547134 | - | - | 0.5090353 | - | - | 0 | IS_MALE:YES | 0.646247 | - | - | 0.4471271 | - | - | 6.02E-251 |
| IS_MI:YES | 0.1044472 | - | - | 0.066129 | - | - | 1.76E-32 | IS_MI:YES | 0.0915483 | - | - | 0.0227154 | - | - | 0 |
| IS_PAD:YES | 0.0284998 | - | - | 0.0173361 | - | - | 6.39E-11 | IS_PAD:YES | 0.0254226 | - | - | 0.0068033 | - | - | 5.47E-79 |
| IS_PULMONARY_DISEA | 0.0665519 | - | - | 0.0404509 | - | - | 2.77E-24 | IS_PULMONARY_DISEA | 0.0622042 | - | - | 0.0231529 | - | - | 2.26E-105 |
| IS_SMOKING:YES | 0.1192108 | - | - | 0.1244107 | - | - | 0.00051 | IS_SMOKING:YES | 0.1340095 | - | - | 0.1061625 | - | - | 1.6TE-14 |
| IS_STROKE_TIA:YES | 0.0559035 | - | - | 0.0368533 | - | - | 7.73E-15 | IS_STROKE_TIA:YES | 0.0498986 | - | - | 0.0114645 | - | - | 2.31E-129 |
| IS_SYSTEMIC_ATHEROS | 0.0284998 | - | - | 0.0173361 | - | - | 6.39E-11 | IS_SYSTEMIC_ATHEROS | 0.0254226 | - | - | 0.0068033 | - | - | 5.47E-79 |
| IS_THYROTOXICOSIS:YE | 0.0093956 | - | - | 0.0112501 | - | - | 0.18787 | IS_THYROTOXICOSIS:YE | 0.0089249 | - | - | 0.0094005 | - | - | 0.719163222 |
| IS_VALVULAR_DISEASE: | 0.0341372 | - | - | 0.0118422 | - | - | 1.90E-53 | IS_VALVULAR_DISEASE: | 0.0305612 | - | - | 0.006463 | - | - | 7.36E-136 |
| IS_WHITE:YES | 0.9668024 | - | - | 0.9405791 | - | - | 2.91E-18 | IS_WHITE:YES | 0.9688979 | - | - | 0.9476849 | - | - | 4.54E-16 |
| SBP_AT_INDEX_DATE | 144.34899 | 19.554330 | 6380 | 144.52849 | 19.205944 | 133421 | 0.35782 | SBP_AT_INDEX_DATE | 143.45380 | 19.332788 | 7395 | 138.99548 | 18.007358 | 431998 | 3.01E-02 |
| WEIGHT_AT_INDEX_DA | 86.050846 | 17.84069 | 6366 | 81.632936 | 16.679861 | 133421 | 1.23E-87 | WEIGHT_AT_INDEX_DA | 85.421663 | 17.773569 | 7395 | 77.720218 | 15.681487 | 431998 | 0 |

FIG. 3

INTERACTIVE SUBGROUP DISCOVERY

BACKGROUND

The present invention relates to the electrical, electronic, and computer arts, and more specifically, to improvements of machine learning models for classifying "big data."

Machine learning models are applicable to "big data" in many settings. "Big data" generally means data sets too large to be tractable or comprehensible by human analysts. Machine learning can identify subgroups in big data that enhance the human analysts' understanding of the data. However, sometimes machine learning falls short in identifying meaningful subgroups in the data. For example, machine learning is not sensitive to sampling bias in data sets. Thus, sometimes subgroups identified by machine learning models only amplify the inherent bias of the underlying data.

SUMMARY

Principles of the invention provide techniques for interactive subgroup discovery. In one aspect, an exemplary computer-implemented method includes obtaining covariates and an outcome data for a population, and partitioning the population into a plurality of subgroups. The method further includes producing outcomes predictions by applying a machine learning model to the covariate data for the population; computing performance measures for each subgroup based on the outcomes predictions and outcome data; comparing the performance measures for at least one subgroup to the performance measures for at least one other subgroup; and identifying an outlying subgroup for which the performance measures are different than the performance measures for one or more other subgroups.

One or more embodiments of the invention or elements thereof can be implemented in the form of a computer program product including a computer readable storage medium with computer usable program code for facilitating the method steps indicated. Furthermore, one or more embodiments of the invention or elements thereof can be implemented in the form of a system (or apparatus) including a memory that embodies computer executable instructions, and at least one processor that is coupled to the memory and operative by the instructions to facilitate exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a tangible computer readable storage medium (or multiple such media) and implemented on a hardware processor, or (iii) a combination of (i) and (ii); any of (i)-(iii) implement the specific techniques set forth herein.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

In view of the foregoing, techniques of the present invention can provide substantial beneficial technical effects. For example, one or more embodiments provide:

The ability to interact with any type of observational data.

Interaction with a data frame through a user interface could be useful to identify subgroups with unique characteristics to explore further.

Additionally, a user can gather knowledge that a classifier (i.e., a machine learning trained model) performs unexpectedly well or worse for a certain subgroup and be able to explore this group further to understand the underlying reasons for this behavior.

Evaluation of different thresholds for a classifier applied to the subgroup to better understand decision-making.

Rapid interaction with data frames to gather performance insights specific to a selected subgroup.

Ability to incorporate any type of observational data frames into the system and method.

Some embodiments may not have these potential advantages and these potential advantages are not necessarily required of all embodiments. These and other features and advantages of the present invention will become apparent from the following detailed description of illustrative embodiments thereof, which is to be read in connection with the accompanying drawings.

BRIEF DESCRIPTION OF THE DRAWINGS

FIG. 3 depicts a table of statistical data for a subgroup and for an entire data set.

DETAILED DESCRIPTION

One or more embodiments provide a mixed-initiative approach for subgroup discovery. We have found that incorporating human intelligence interactively into a data discovery mechanism helps in identifying sub-groups in which the functionality of machine learning models yields an improved performance. One or more embodiments automatically identify subgroups by using at least one of: a data-driven (mining algorithms) approach; or a knowledge-driven (manually-defined stratification) approach. In one or more embodiments, users can inspect details of subgroups by exploring their feature distributions. Additionally, in one or more embodiments, users can provide feedback to refine subgroups. For example, users can "keep" subgroups they like; users can run discovery for subpopulation(s); users can manually choose different prediction thresholds for a model and observe how it affects performance and fairness measures; and/or, users can view the characteristics of a model (classification/regression/time-to-event) for the subgroups, separately. Characteristics of a model include discrimination (i.e., how well the model distinguishes outcomes), calibration (i.e., to what extent discrimination is under or over-estimated; a calibration value of 1.0 means a well-calibrated classifier applicative to the population or subpopulation; values below 1.0 indicate an over estimation of the risk and values above 1.0 indicate an under-estimation), and/or prevalence (i.e., percentage of the population with a certain characteristic; for example, male prevalence of 48.0% means that 48.0% of the population are males, heart failure prevalence of 3.0% means that 3.0% of the population have a history of heart failure and the rest, 97.0%, are free of heart failure). In one or more embodiments, users can explore a specific subpopulation created on the fly (e.g., "Table 300" as shown in FIG. 1).

Figure 1:
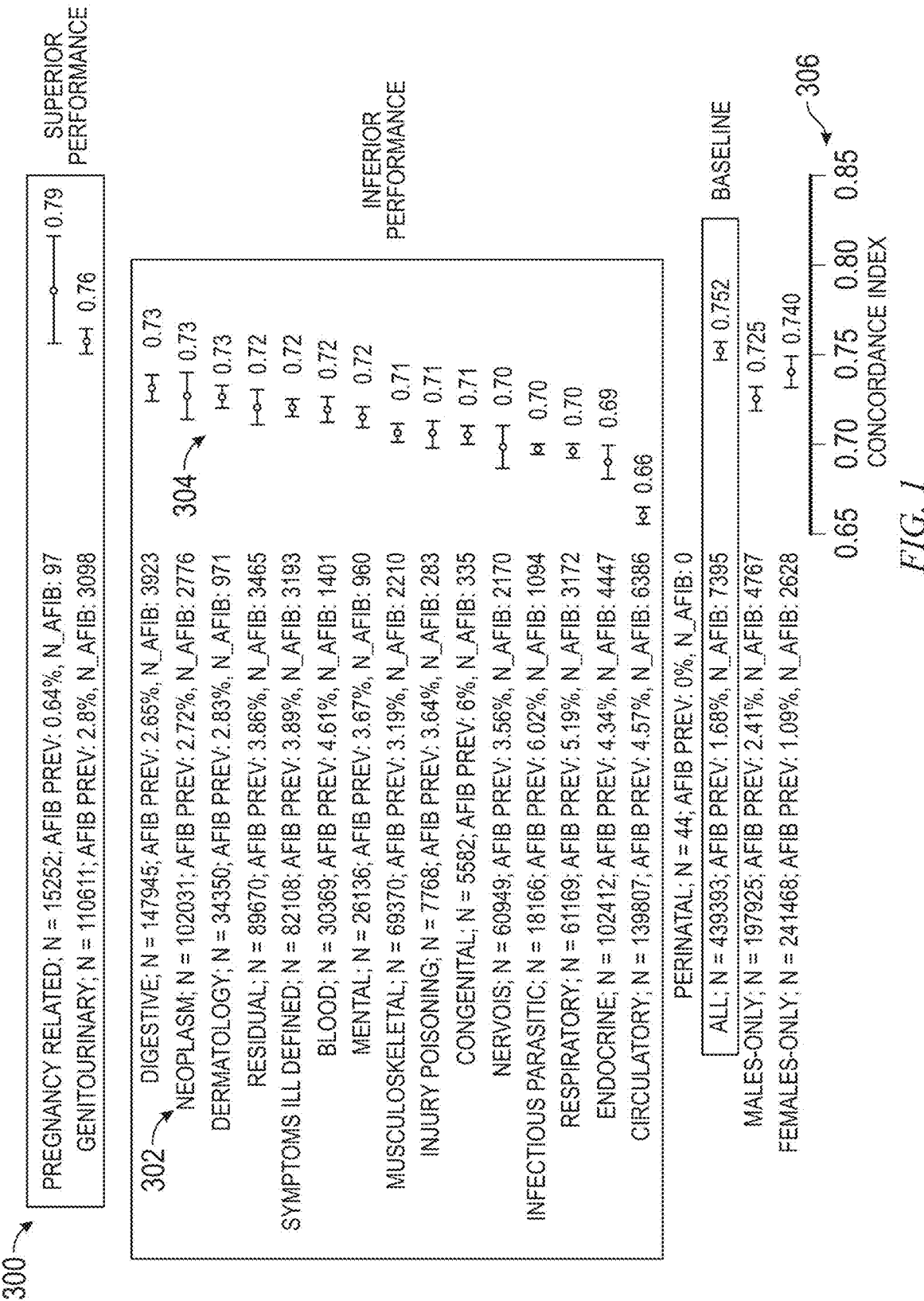
FIG. 1 depicts a table of medical diagnoses and concordance index values for a machine learning model predicting an outcome based on patient data.

With continued reference to FIG. 1, Table 300 has two columns. The left column 302 shows a listing of subgroups. The right column 304 shows a "concordance index" 306 that measures the accuracy of a machine learning model for predicting a variable of interest for the members of each subgroup. In the example of Table 300, the subgroups are combinations of medical diagnoses or "comorbidities" that are diagnosed at or before the beginning of a study period, and the variable of interest is presence or absence of atrial fibrillation within the study period of five years following the beginning of the study. Interestingly, the "circulatory" subgroup exhibits the worst accuracy for predicting atrial fibrillation, which is a cardiac symptom that one might intuitively associate with the circulatory system. The poor accuracy for the circulatory subgroup suggests a variety of possibilities to explore. For example, it could be that the poor performance is derived from low variance of characteristics of this subpopulation thus limiting prediction performance. A possible direction to address would be to incorporate additional covariates into the prediction mechanisms, for example, applicative to the heart such as ejection fraction values, or covariates extracted from Echocardiogram (Echo) reports related to the functionality of the heart. Another possibility would be for the user to keep interacting with the system to identify subsets in the circulatory subgroup with a possibility to increase performance without modifying the classifier (e.g., patients with specific cardiovascular diseases, different age ranges, gender differences, demographic differences, different zip codes). The user can also rapidly assess performance in data frames focused on circulatory conditions derived from other databases to explore if the reduced or increased performance is specific to a certain database or is more broadly impacted.

In response to the sort of disparity in accuracy as shown in FIG. 1, in one or more embodiments, users can interactively and/or automatically generate and refine subgroups. In one or more embodiments, interactive visualizations communicate the process of defining subgroups so that users can inspect subgroup details. Accordingly, domain experts and data scientists can refine subgroups so that they can iteratively find subgroups of interest (e.g., highly predictable, well-calibrated). Without leaving a subgroup discovery system 96 (see FIGS. 7 and 9), users can visualize machine learning model performances on subgroups (e.g., concordance index, area under the curve, calibration). The system 96 can identify, in groups known to be under-performing (e.g., circulatory diagnosis), subgroups that could be better performing (e.g., subgroups with specific characteristics) as presented in a descending order in FIG. 1 as well as compared to the population as a whole ("Baseline").

Figure 2:
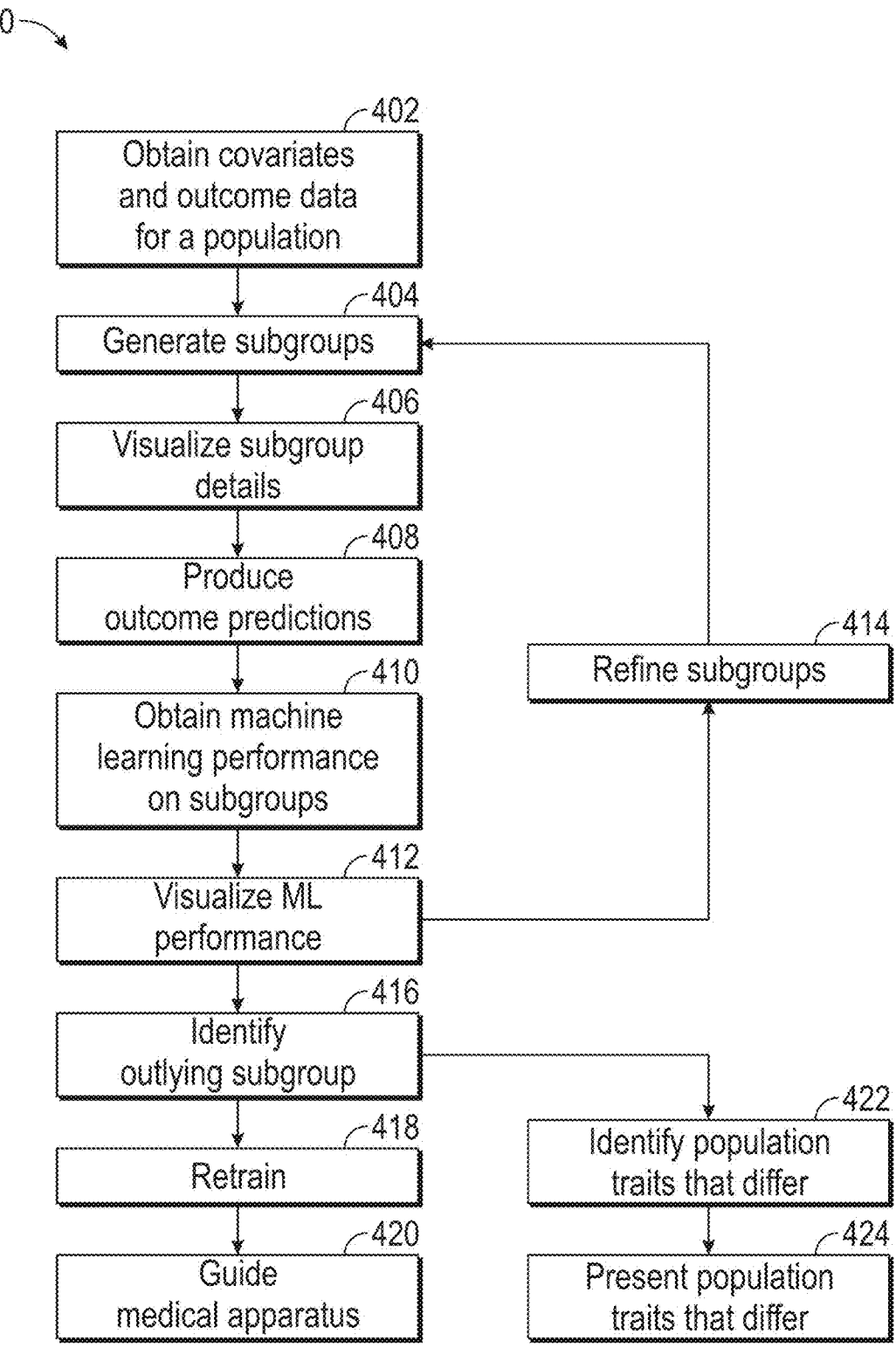
FIG. 2 depicts a flowchart of a method implemented according to an exemplary embodiment.

Thus, in order to carry out embodiments of the invention, the system 96 implements a method 400, as shown in FIG. 2. At 402, obtain covariates and an outcome data for a population. At 404, generate subgroups of the population by partitioning the population into a plurality of subgroups. In one or more embodiments, subgroups can be generated using conventional population stratification approaches (defined by domain knowledge). In one or more embodiments, subgroups can be defined by: one or more comorbidities; a combination of covariates (e.g., patient characteristics and comorbidities); widely used disease classification mechanisms (e.g., Clinical Classifications Software [CCS] classes); patient behavioral characteristics (e.g., smoking status, nonadherence). In one or more embodiments, subgroups can be defined by algorithmic-based methods (e.g., clustering techniques). Possible clustering algorithms include k-means, agglomerative hierarchical clustering, density-based spatial clustering of applications with noise, gaussian mixture model, and the like. At 406, visualize subgroup details. At 408, produce outcomes predictions by applying a machine learning model to the covariate data for the population. At 410, obtain machine learning performance on subgroups, e.g., by querying an existing database or by computing performance measures for each subgroup based on the outcomes data and outcomes predictions. In one or more embodiments, the performance measures may include model performance metrics such as prediction accuracy, concordance index, area under the curve, calibration, standardized hazard ratios. In one or more embodiments, the performance measures may include bias and fairness metrics such as statistical parity difference, true positive rate difference, true negative rate difference.

Figure 4:
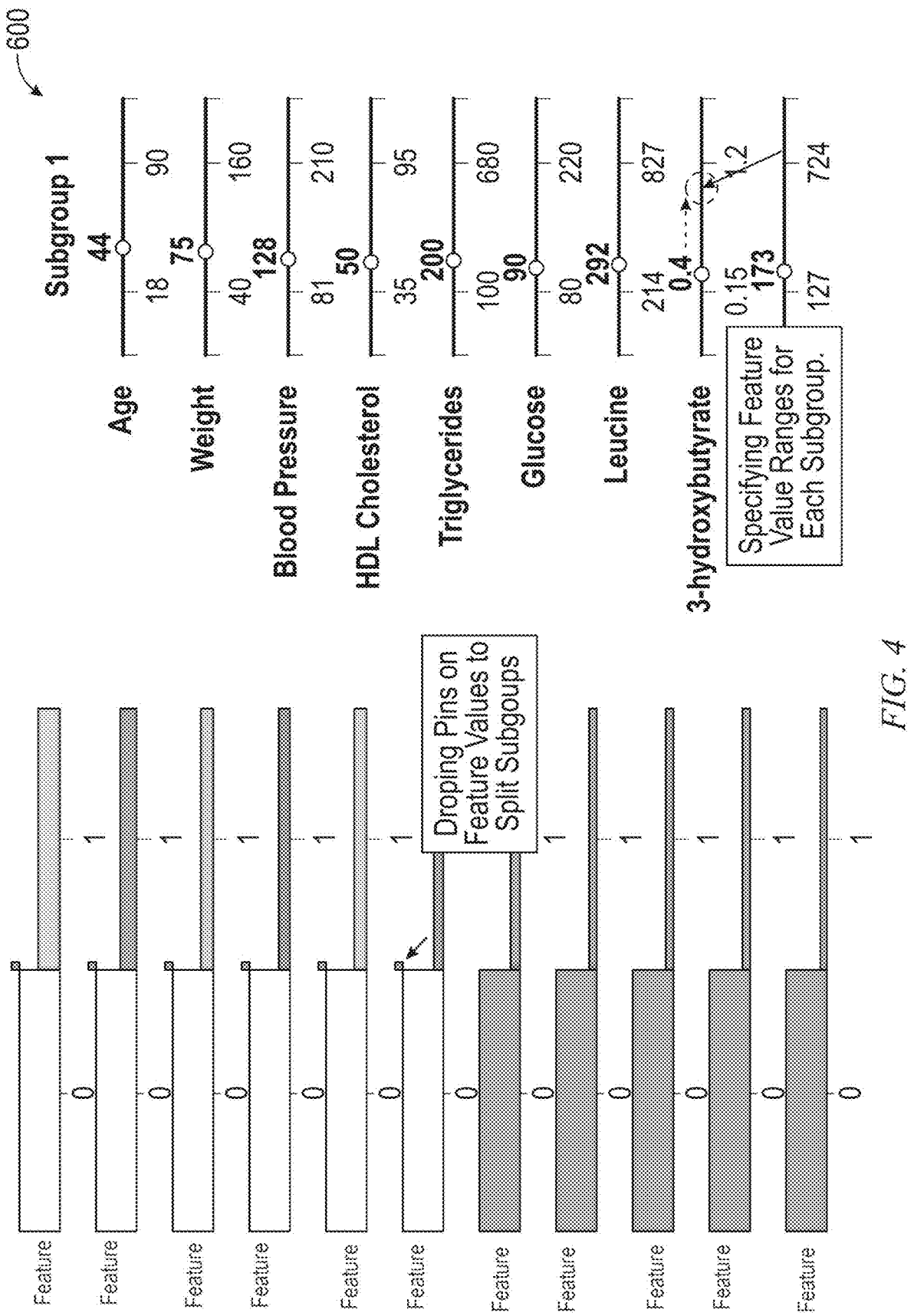
FIG. 4 depicts a subgroup diagram, according to an exemplary embodiment.
Figure 5:
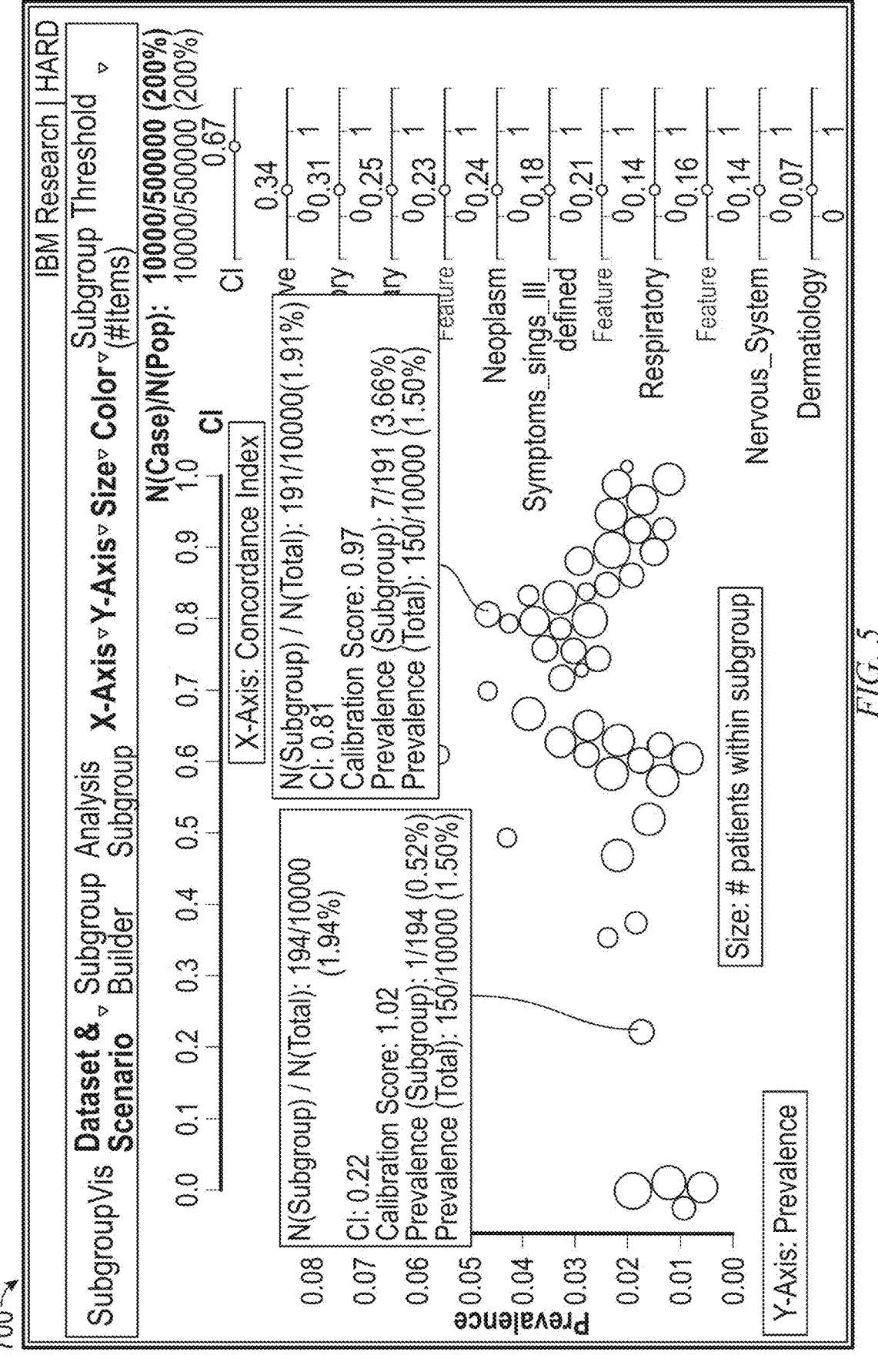
FIG. 5 depicts a summary of subgroups, according to an exemplary embodiment.
Figure 6:
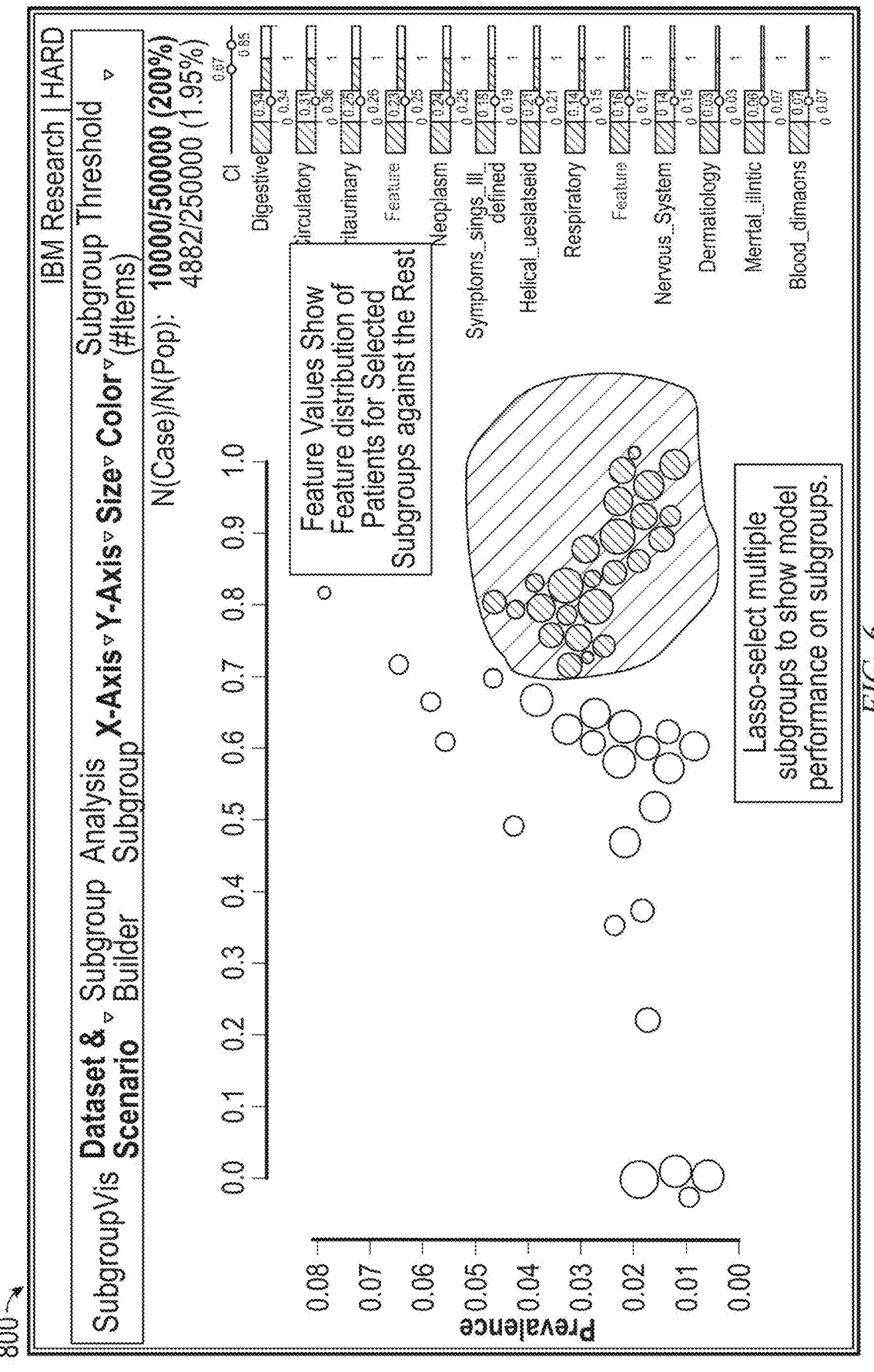
FIG. 6 depicts an interactive summary of subgroups, according to an exemplary embodiment.

At 412, visualize machine learning performance on subgroups using scatter plots as in FIG. 5 and FIG. 6. At 414, refine subgroups using an interface similar to that shown in FIG. 4, where a user can adjust sliders to select a subgroup of individuals who are indicated with documented endocrinology conditions. The system then presents to the user, for this group, a variety of performance and fairness metrics. The user can then refine the subgroup further—for example, add a constraint in which in additional to endocrinology conditions, the subgroup is indicated with two more CCS-defined conditions—circulatory and digestive. This pin-drop process, accomplished on the left-hand scales of an interface as shown in FIG. 4, produces a smaller subgroup for which performance and fairness metrics are calculated and presented in real-time. The user then can compare the metrics between the two groups to gather insights on whether patients with the two additional conditions perform differently compared to the healthier group.

At 414, the system 96 allows users to refine subgroups by interactively adjusting the distribution of variables for subgroups using user interface elements (e.g., slider, dropdown menu). Each subgroup is characterized by a visualization of the distribution of variables (e.g., age 45-49). Users can adjust the range of values (for continuous variables) or select values (for discrete variables) using the interactive visualization. As the subgroup definition is updated by user's interaction (as in 404), the system applies the underlying machine learning model to the updated subgroup (as in 408) and presents the newly updated model performances for the subgroup (as in 412).

At 416, the system 96 identifies an outlying subgroup for which the performance measures are different than the performance measures are for one or more other subgroups.

At 418, the system 96 may retrain the machine learning model on additional covariate and outcomes data for the outlying subgroup.

At 420, the system 96 may guide a medical apparatus in assessing and/or treating a member of the outlying subgroup for a medical condition in response to the retrained machine learning model predicting an outcome for that member.

One or more embodiments, at 422, identify population traits that differ in the outlying subgroup compared to other subgroups; and, at 424, present, to a user, the population traits which differ, to indicate bias may exist in the outlying subgroup. In other words, the system 96 may generate statistical analyses for each subgroup to help compare the subgroups to each other and/or to an overall population (e.g., "Table 500" as shown in FIG. 3). Table 500 contains 2 sub tables: to the left is a summary for the subgroup of 139,807 patients with circulatory conditions (as defined by CCS); to the right is a summary for the population considered as a whole (439,393 patients). Each sub table contains statistical results to compare the positive (develop the predicted condition) and negative (free of the predicted condition) patients considered. Each row represents the result of a statistical analysis applied to a single covariate (e.g., t-test, chi-square test). Each table has 8 columns: the leftmost indicates a variable/covariate name. The next 3 columns (from left to right) summarize the positive population ("YES") and the next 3 columns (again, from left to right) represent the negative population ("NO"). Values include mean or prevalence (depends on the variable), standard deviation, and optionally, total number of patients. The 8th column is a P value calculation indicating a statistical difference or the lack of a statistical difference for the population (or sub-population) within the context of the covariate. Such summary tables are often referred in the scientific literature as "Table 1" and the statistical tests are often referred to as "univariate analyses". As an example, in the left-hand table presented ("Circulatory"; 139,807 patients), for the covariate "is_male"—the values indicate that 65.4% of the positive patients in the circulatory subgroup (4,181 of 6,386 patients) are males (2,205 are females).

It further shows that 50.9% of the negative patients in the circulatory subgroup (67,916 of 133,421 patients) are males (65,505 are females). The P value for this covariate indicates a statistically significant difference (P<0.001). As another example, "SBP" (systolic blood pressure) indicates no statistical significance between the positive and negative patients of the circulatory subgroup with 144.34 compared to 144.53 (P=0.358). Looking at SBP difference in the whole population (the right sub table) indicates that there is a statistically significant difference between the positive and negative patients with 143.45 compared to 138.99 (P<0.001). This finding indicates a low variability between positive and negative patients in the circulatory subgroup, and a high variability when the difference is evaluated considering the population as a whole. Such information presented in real-time to the users helps understanding which covariates may be more predictive than others within the context of the explored subgroup—in this example SBP could be highly predictive when the population is being evaluated as a whole, but has a limited predictive power when applied to the circulatory subgroup.

In one or more embodiments, the interface enables a user to generate novel subgroups by dropping pins on feature values of a subgroup. For example, FIG. 4 shows a diagram

600 of a Subgroup 1 that includes subgroups first defined by some "other" demographic variables. The distribution of other comorbidity variables is summarized by the mean value for the subgroup on the right side. Also, continuous variables could be used to refine a subgroup, such as weight, height, blood pressure and various risk scores (e.g., CHARGE-AF, EHR-AF). For example, FIG. 4 shows how users can update the threshold of 3-hydroxybutyrate by dragging the slider to the right. Likewise, users can directly specify the value ranges for the target variable to update the definition of the subgroup.

FIG. 5 shows a summary 700 of all subgroups in two-dimensional space, where x-axis is concordance index (model discrimination index in analysis involving survival time data) and y-axis is prevalence (the proportion of patients with the outcome case to all). The size of each subgroup circle represents the number of patients belong to the subgroup. Using this view, users can overall inspect the distribution of subgroups over the given two dimensions, which can be selected via the dropdown menu located at the top area. When users hover over each subgroup, a popup dialog provides more detailed information about the subgroup, such as Calibration Score.

FIG. 6 shows an interactive summary 800 with which users can interactively merge subgroups on the view. Users can select multiple subgroups scattered on the two-dimensional space by drawing an enclosed shape surrounding the target subgroups (i.e., lasso-selection). Users can continue forming groups of subgroups by using this feature. Then, the system assigns distinct color for each group defined by users and generates summary of the subgroup by showing the distribution over variables using the color, as shown on the right side. Using this feature, users can interactively discover ways to group patients by combining and merging multiple subgroups.

One or more embodiments allow users to assess, for any selected subgroup, measures related to fairness, such as statistical parity difference, true positive rate difference, and true negative rate difference. A user, for example, can quickly explore different demographics to assess if there are biases or lack of biases. A bias can be measured by difference values of the fairness-related metrics from the optimal value. For example, the ideal value indicating no bias for the statistical parity difference metric is 0.0—this means that given a pre-defined fairness variable to assess (often called "protected" variable), there is no difference between the probability of outcome for two classes of patients (e.g., a certain demographic). Other common fairness-related metrics include sensitivity and specificity differences.

Figure 7:
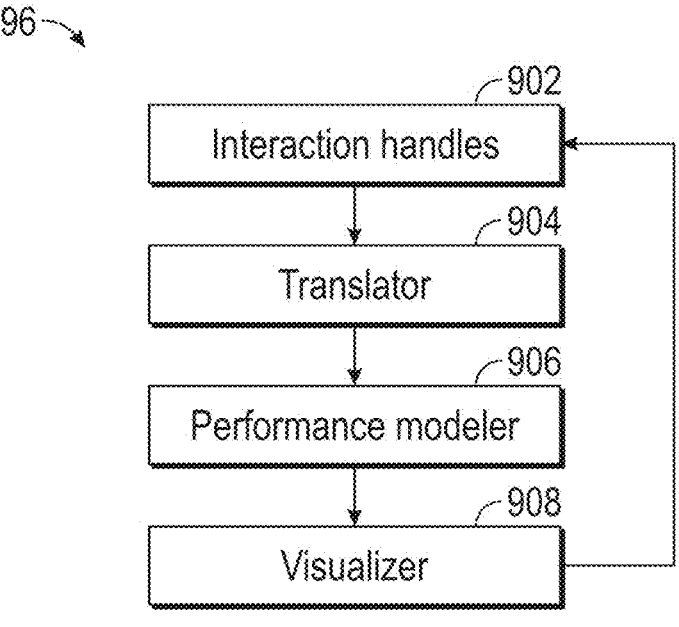
FIG. 7 depicts a system for implementing the method of FIG. 2.

To implement the ability in a visualization system, one or more embodiments employ a backend functionality 96, as shown in FIG. 7, to generate the model performance results by applying the model to the updated subgroup. The backend functionality 96 includes interaction handles 902, a translator 904, a performance modeler 906, and a visualizer 908. Once a user changes the definition of a subgroup by adjusting feature values of the subgroup using the interaction handles 902, such as slider, dropdown menu, or visualization itself, the translator 904 instantly translates the users' interaction into the database query to select the relevant subgroups of patients, the performance modeler 906 generates the model performance results of the subgroups, and the visualizer 908 updates the visualizations with the new results. As users refine subgroups by modifying the feature value ranges, the backend functionality keeps track of the changes made and selects relevant patients that satisfy the conditions for each subgroup. The ability can be extended to discover new subgroups collaboratively among multiple users. Once computer algorithms discover and display subgroups, users can update them. Users can also preselect some desired ranges for variables, so the computer algorithms can use the information to narrow down the search space for target subgroups.

Thus, one or more embodiments provide a user with an ability to interact with any type of observational data. For example, in a medical scenario, a user can upload a data frame that contains covariates, an outcome, and a machine learning trained model. The covariates could be laboratory values, comorbidities, vitals, medications, demographic details, genetic information, data incorporated from wearables, from smart pills, questionnaires, and the like. The outcome could be an onset of a disease (e.g., atrial fibrillation within the subsequent 5 years after a pre-defined date), an event (e.g., 30-day re-admission, 90-day mortality), an uncontrolled lab value for a disease (e.g., hemoglobin A1C for diabetes, blood pressure for hypertension).

The user then can interact with a data frame through a user interface to identify subgroups that could be of an interest to explore further. The identification involves the use of machine learning algorithms applied to each selected subgroup, accompanied by calculations of a variety of measures (e.g., performance-related such as concordance index, and the area under the curve; fairness-related such as statistical parity difference, true positive difference rate, true negative difference rate). The methods are model-agnostic, so any machine learning algorithms can be used, such as deep learning algorithms, random forest, decision tree, gradient boosting, etc.

A user can learn, for example, that a classifier (i.e., a machine learning trained model) performs unexpectedly well or worse for a certain subgroup and explore this group further to understand the underlying reasons for this behavior.

A user also can evaluate different thresholds for a classifier applied to the subgroup to better understand a physician's decision-making mechanism within the context of risk thresholds proposed in official clinical guidelines (e.g., a threshold to initiate statins).

Additionally, a user can rapidly interact with data frames to gather performance insights specific to a selected subgroup, which could be beneficial towards understanding existing prediction models. A prediction model has the form of one or more equations capable of assessing risk of a future medical condition, for example, an on-set of a disease, a re-admission, a significant change in a laboratory observation, as well as mortality.

Another advantage is a user's ability to incorporate any type of observational data frames into the system and method. For example, financial-related, in which the classifier could be prediction mechanisms such as consumer credit risk scores, or education-related where the prediction mechanism would be a score such as a standardized placement or admission test score.

Given the discussion thus far, it will be appreciated that, in general terms, an exemplary computer-implemented method, according to an aspect of the invention, includes obtaining covariates and an outcome data for a population, and partitioning the population into a plurality of subgroups. The method further includes producing outcomes predictions by applying a machine learning model to the covariate data for the population; computing performance measures for each subgroup based on the outcomes predictions and outcome data; comparing the performance measures for at least one subgroup to the performance measures for at least one other subgroup; and identifying an outlying subgroup for which the performance measures are different than the performance measures for one or more other subgroups.

In one or more embodiments, the method also includes retraining the machine learning model on additional covariate and outcomes data for the outlying subgroup.

In one or more embodiments, the method also includes assessing and/or treating a member of the outlying subgroup for a medical condition in response to the retrained machine learning model predicting an outcome for that member.

In one or more embodiments, the method also includes identifying population traits that differ in the outlying subgroup compared to other subgroups; and presenting, to a user, the population traits which differ, to indicate bias may exist in the outlying subgroup.

In one or more embodiments, the method also includes partitioning the population by applying a clustering algorithm to the population.

In one or more embodiments, the method also includes partitioning the population by applying domain expert knowledge to the population.

In one or more embodiments, the method also includes comparing the outcomes predictions for the at least one subgroup to the outcomes predictions for other subgroups or the entire population.

In one or more embodiments, the performance measures include model performance metrics such as prediction accuracy, concordance index, area under the curve, calibration, standardized hazard ratios. In one or more embodiments, the performance measures include bias and fairness metrics such as statistical parity difference, true positive rate difference, true negative rate difference.

Figure 10:
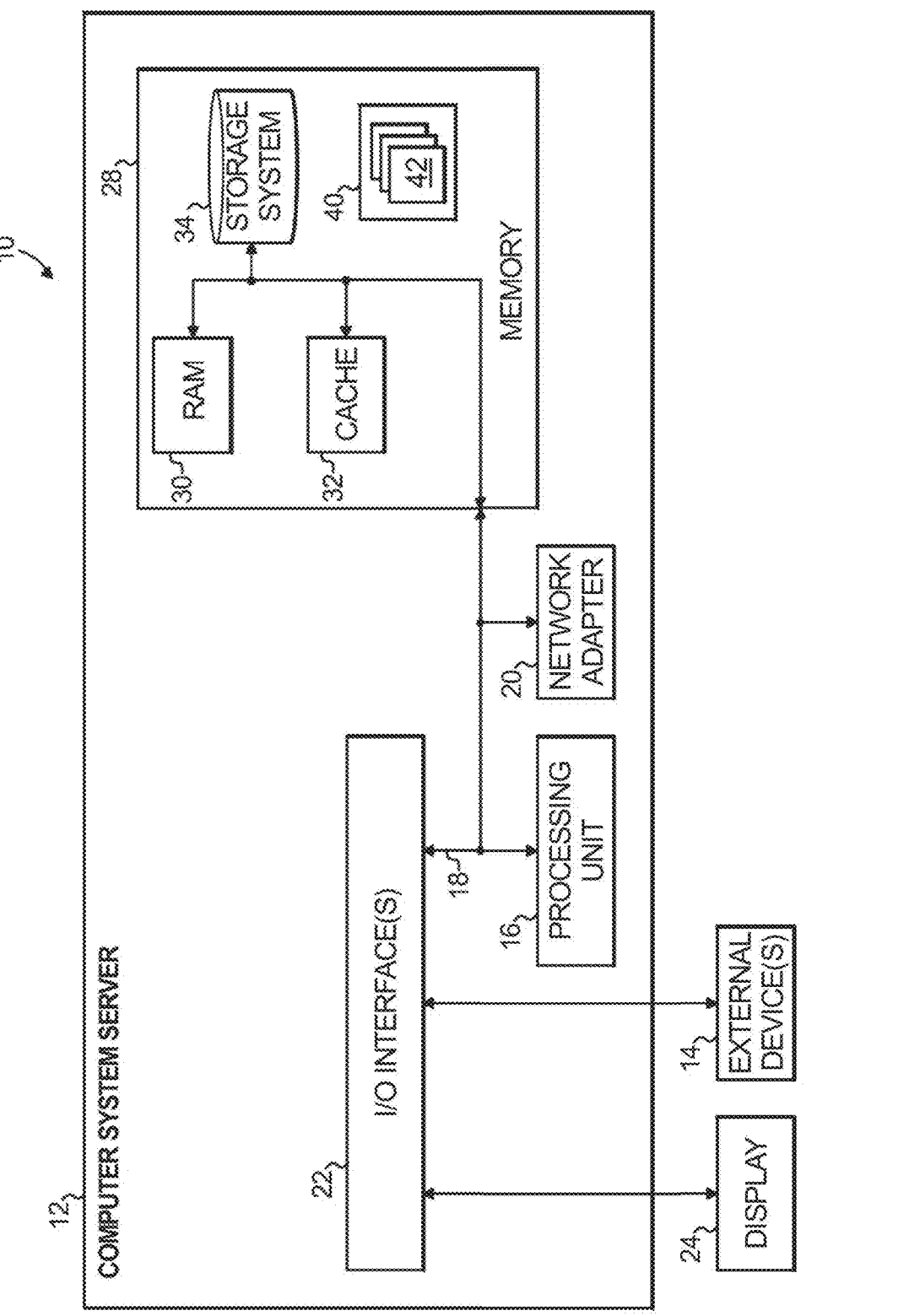
FIG. 10 depicts a computer system that may be useful in implementing one or more aspects and/or elements of the invention, also representative of a cloud computing node according to an embodiment of the present invention.

One or more embodiments of the invention, or elements thereof, can be implemented in the form of an apparatus including a memory and at least one processor that is coupled to the memory and operative to perform exemplary method steps, or in the form of a non-transitory computer readable medium embodying computer executable instructions which when executed by a computer cause the computer to perform exemplary method steps. FIG. 10 depicts a computer system that may be useful in implementing one or more aspects and/or elements of the invention, also representative of a cloud computing node according to an embodiment of the present invention.

Referring now to FIG. 10, cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, and external disk drive arrays, RAID systems, tape drives, and data archival storage systems, etc.

Thus, one or more embodiments can make use of software running on a general purpose computer or workstation. With reference to FIG. 10, such an implementation might employ, for example, a processor 16, a memory 28, and an input/output interface 22 to a display 24 and external device(s) 14 such as a keyboard, a pointing device, or the like. The term "processor" as used herein is intended to include any processing device, such as, for example, one that includes a CPU (central processing unit) and/or other forms of processing circuitry. Further, the term "processor" may refer to more than one individual processor. The term "memory" is intended to include memory associated with a processor or CPU, such as, for example, RAM (random access memory) 30, ROM (read only memory), a fixed memory device (for example, hard drive 34), a removable memory device (for example, diskette), a flash memory and the like. In addition, the phrase "input/output interface" as used herein, is intended to contemplate an interface to, for example, one or more mechanisms for inputting data to the processing unit (for example, mouse), and one or more mechanisms for providing results associated with the processing unit (for example, printer). The processor 16, memory 28, and input/output interface 22 can be interconnected, for example, via bus 18 as part of a data processing unit 12. Suitable interconnections, for example via bus 18, can also be provided to a network interface 20, such as a network card, which can be provided to interface with a computer network, and to a media interface, such as a diskette or CD-ROM drive, which can be provided to interface with suitable media.

Accordingly, computer software including instructions or code for performing the methodologies of the invention, as described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

A data processing system suitable for storing and/or executing program code will include at least one processor 16 coupled directly or indirectly to memory elements 28 through a system bus 18. The memory elements can include local memory employed during actual implementation of the program code, bulk storage, and cache memories 32 which provide temporary storage of at least some program code in order to reduce the number of times code must be retrieved from bulk storage during implementation.

Input/output or I/O devices (including but not limited to keyboards, displays, pointing devices, and the like) can be coupled to the system either directly or through intervening I/O controllers.

Network adapters 20 may also be coupled to the system to enable the data processing system to become coupled to other data processing systems or remote printers or storage devices through intervening private or public networks. Modems, cable modem and Ethernet cards are just a few of the currently available types of network adapters.

As used herein, including the claims, a "server" includes a physical data processing system (for example, system 12 as shown in FIG. 10) running a server program. It will be understood that such a physical server may or may not include a display and keyboard.

Figure 8:
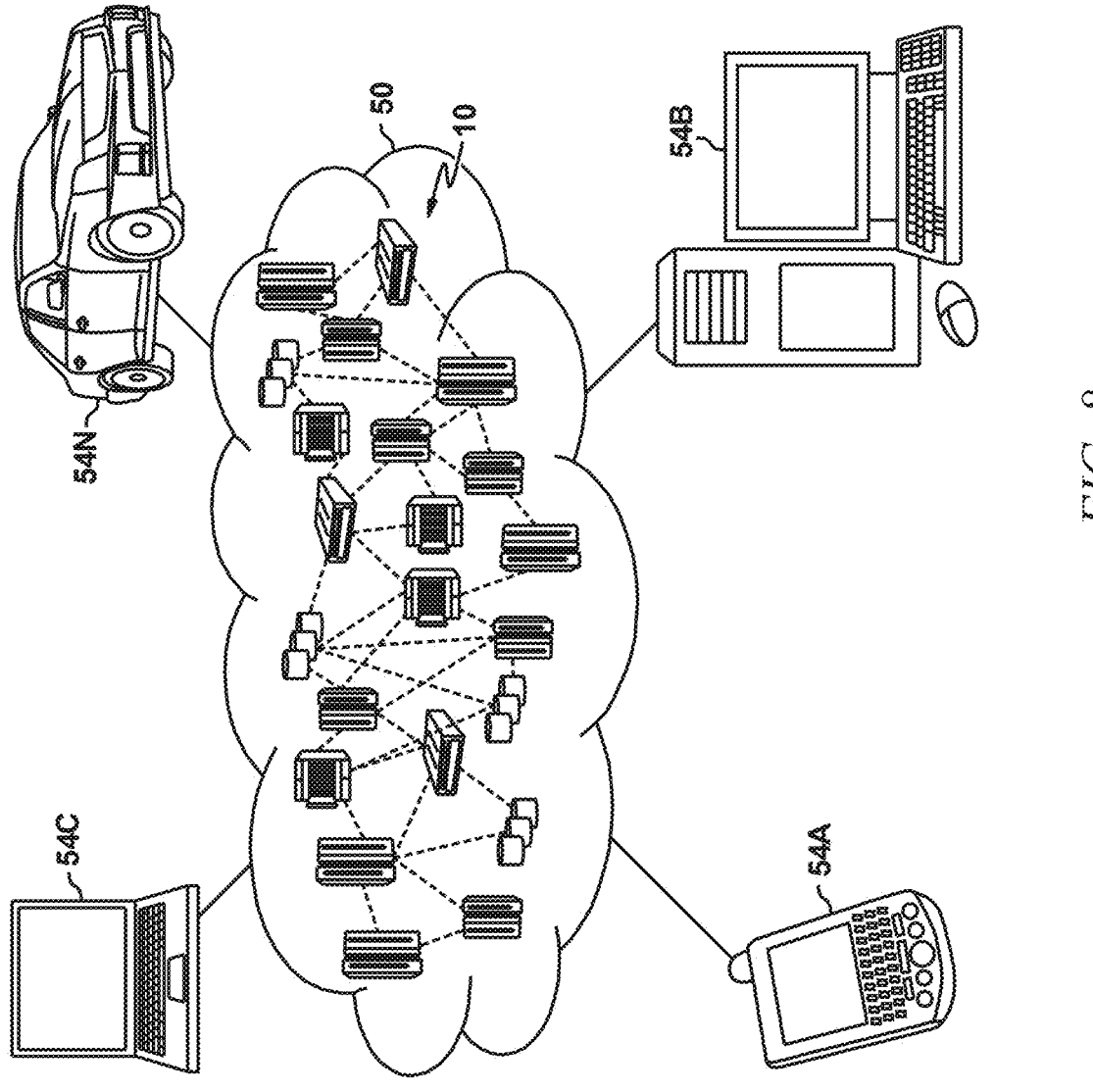
FIG. 8 depicts a cloud computing environment according to an embodiment of the present invention.

One or more embodiments can be at least partially implemented in the context of a cloud or virtual machine environment, although this is exemplary and non-limiting. Reference is made to FIGS. 7-8 and accompanying text.

It should be noted that any of the methods described herein can include an additional step of providing a system comprising distinct software modules embodied on a computer readable storage medium; the modules can include, for example, any or all of the appropriate elements depicted in the block diagrams and/or described herein; by way of example and not limitation, any one, some or all of the modules/blocks and or sub-modules/sub-blocks described. The method steps can then be carried out using the distinct software modules and/or sub-modules of the system, as described above, executing on one or more hardware processors such as 16. Further, a computer program product can include a computer-readable storage medium with code adapted to be implemented to carry out one or more method steps described herein, including the provision of the system with the distinct software modules.

One example of user interface that could be employed in some cases is hypertext markup language (HTML) code served out by a server or the like, to a browser of a computing device of a user. The HTML is parsed by the browser on the user's computing device to create a graphical user interface (GUI).

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 8, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 8 are intended to be illustrative only and that computing nodes 10 and cloud computing environment 50 can communicate with any type of computerized device over any type of network and/or network addressable connection (e.g., using a web browser).

Figure 9:
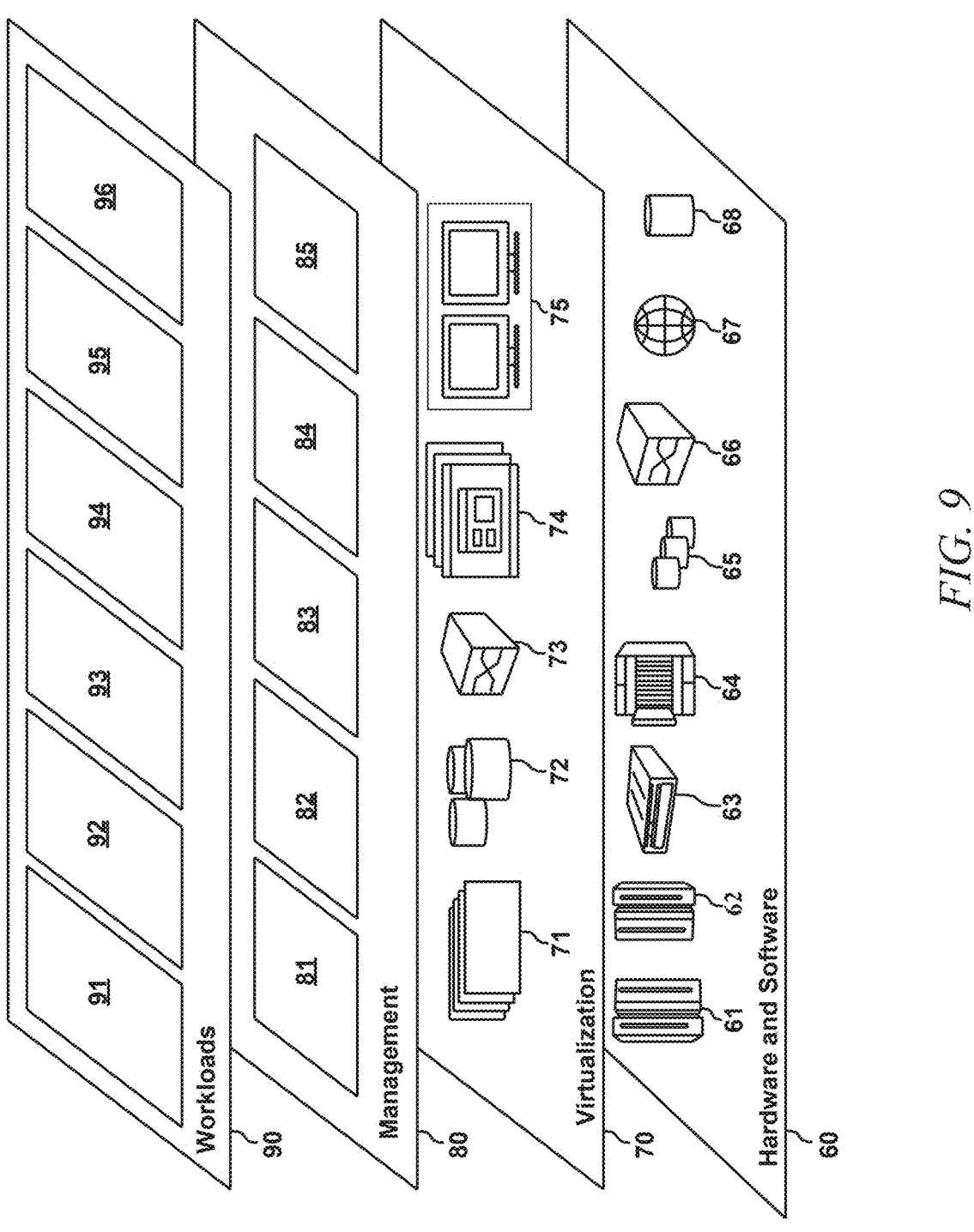
FIG. 9 depicts abstraction model layers according to an embodiment of the present invention.

Referring now to FIG. 9, a set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and at least a portion of the subgroup discovery system 96.

Exemplary System and Article of Manufacture Details

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for assessing a risk to a subpopulation of a medical condition, the method comprising:

obtaining covariates and an outcome data for a population;

partitioning the population into a plurality of subgroups, wherein each subgroup is a different comorbidity that is predictive of the medical condition;

producing outcome predictions by applying a machine learning model to the covariate data for the population;

computing performance measures of the machine learning model for each subgroup based on the outcomes predictions and the outcome data;

comparing the performance measures for at least one subgroup to the performance measures for at least one other subgroup, including producing an interactive visualization of machine learning performance of the machine learning model for each of the subgroups, wherein the visualization is displayed by a user interface, wherein the performance measures include a concordance index that measures an accuracy of the machine learning model for predicting the risk of the medical condition and a fairness metric;

identifying an outlying subgroup for which the concordance index is different than the concordance index for one or more other subgroups;

receiving, through the interactive visualization, input indicative of a modified definition of the outlying subgroup;

tracking changes in the modified definition;

computing, in real-time, updated model performance results by applying the machine learning model to the outlying subgroup based on the modified definition; and updating the visualization of the machine learning performance of the machine learning model, including the concordance index and the fairness metric, for each of the subgroups.

2. The method of claim 1 further comprising:

retraining the machine learning model on additional covariate and outcomes data for the outlying subgroup.

3. The method of claim 1 further comprising:

guiding a medical apparatus in treating a member of the outlying subgroup for the medical condition in response to the retrained machine learning model predicting an outcome for that member.

4. The method of claim 1 further comprising:

identifying population traits that differ in the outlying subgroup compared to other subgroups; and presenting, through the interactive visualization, to a user, the population traits which differ, to indicate bias in the outlying subgroup.

5. The method of claim 1, further comprising:

partitioning the population by applying a clustering algorithm to the population.

6. The method of claim 1, further comprising:

partitioning the population by applying domain expert knowledge to the population.

7. The method of claim 1 further comprising comparing the outcome predictions for the at least one subgroup to the outcomes predictions for the entire population.

8. The method of claim 1 wherein the performance measures include model performance metrics including at least one of prediction accuracy, concordance index, area under the curve, calibration, or standardized hazard ratios.

9. The method of claim 1 wherein the performance measures include bias and fairness metrics including at least one of statistical parity difference, true positive rate difference, or true negative rate difference.

10. A computer program product comprising one or more computer readable storage media that embody computer executable instructions, which when executed by a computer cause the computer to perform a method for assessing a risk to a subpopulation of a medical condition, the method comprising:

obtaining covariates and an outcome data for a population;

partitioning the population into a plurality of subgroups, wherein each subgroup is a different comorbidity that is predictive of the medical condition;

producing outcome predictions by applying a machine learning model to the covariate data for the population;

computing performance measures of the machine learning model for each subgroup based on the outcomes predictions and the outcome data;

comparing the performance measures for at least one subgroup to the performance measures for at least one other subgroup, including producing an interactive visualization of machine learning performance of the machine learning model for each of the subgroups, wherein the visualization is displayed by a user interface, wherein the performance measures include a concordance index that measures an accuracy of the machine learning model for predicting the risk of the medical condition and a fairness metric;

identifying an outlying subgroup for which the concordance index is different than the concordance index for one or more other subgroups;

receiving, through the interactive visualization, input indicative of a modified definition of the outlying subgroup;

tracking changes in the modified definition;

computing, in real-time, updated model performance results by applying the machine learning model to the outlying subgroup based on the modified definition; and updating the visualization of the machine learning performance of the machine learning model, including the concordance index and the fairness metric, for each of the subgroups.

11. The computer readable storage medium of claim 10 wherein the method further comprises:

retraining the machine learning model on additional covariate and outcomes data for the outlying subgroup.

12. The computer readable storage medium of claim 10 wherein the method further comprises:

guiding a medical apparatus in treating a member of the outlying subgroup for the medical condition in response to the retrained machine learning model predicting an outcome for that member.

13. The computer readable storage medium of claim 10 wherein the method further comprises:

identifying population traits that differ in the outlying subgroup compared to other subgroups; and presenting, through the interactive visualization, to a user, the population traits which differ to indicate bias may exist in the outlying subgroup.

14. The computer readable storage medium of claim 10 wherein the method further comprises:

partitioning the population by applying a clustering algorithm to the population.

15. The computer readable storage medium of claim 10 wherein the method further comprises:

partitioning the population by applying domain expert knowledge to the population.

16. The computer readable storage medium of claim 10 wherein the method further comprises:

comparing the outcome predictions for the at least one subgroup to the outcomes predictions for the entire population.

17. An apparatus comprising:

a memory embodying computer executable instructions; and at least one processor, coupled to the memory, and operative by the computer executable instructions to perform a method for assessing a risk to a subpopulation of a medical condition, the method comprising:

obtaining covariates and an outcome data for a population;

partitioning the population into a plurality of subgroups, wherein each subgroup is a different comorbidity that is predictive of the medical condition;

producing outcome predictions by applying a machine learning model to the covariate data for the population;

computing performance measures of the machine learning model for each subgroup based on the outcomes predictions and the outcome data;

comparing the performance measures for at least one subgroup to the performance measures for at least one other subgroup, including producing an interactive visualization of machine learning performance of the machine learning model for each of the subgroups, wherein the visualization is displayed by a user interface, wherein the performance measures include a concordance index that measures an accuracy of the machine learning model for predicting the risk of the medical condition and a fairness metric;

identifying an outlying subgroup for which the concordance index is different than the concordance index for one or more other subgroups;

receiving, through the interactive visualization, input indicative of a modified definition of the outlying subgroup;

tracking changes in the modified definition;

computing, in real-time, updated model performance results by applying the machine learning model to the outlying subgroup based on the modified definition; and updating the visualization of the machine learning performance of the machine learning model, including the concordance index and the fairness metric, for each of the subgroups.

18. The apparatus of claim 17 wherein the method performed by the at least one processor further comprises:

retraining the machine learning model on additional covariate and outcomes data for the outlying subgroup.

19. The apparatus of claim 17 wherein the method performed by the at least one processor further comprises:

identifying population traits that differ in the outlying subgroup compared to other subgroups; and presenting, through the interactive visualization, to a user, the population traits which differ to indicate bias may exist in the outlying subgroup.

20. The apparatus of claim 17 wherein the method performed by the at least one processor further comprises:

partitioning the population by applying a clustering algorithm to the population.

* * * * *